(12) United States Patent
Gründeman et al.

(10) Patent No.: US 6,790,171 B1
(45) Date of Patent: Sep. 14, 2004

(54) METHOD AND DEVICE FOR TRANSVENTRICULAR MECHANICAL CIRCULATORY SUPPORT

(75) Inventors: Paul Frederik Gründeman, Utrecht (NL); Cornelis Wilhelmus Jozef Verlaan, Utrecht (NL); Cornelius Borst, Utrecht (NL); Hendricus Jacobus Mansvelt Beck, Utrecht (NL)

(73) Assignee: Universitair Medisch Cenrum Utrecht, Utrecht (NL)

( * ) Notice: Subject to any disclaimer, the term of this patent is extended or adjusted under 35 U.S.C. 154(b) by 0 days.

(21) Appl. No.: 09/936,224

(22) PCT Filed: Mar. 9, 2000

(86) PCT No.: PCT/NL00/00157
§ 371 (c)(1),
(2), (4) Date: Mar. 1, 2002

(87) PCT Pub. No.: WO00/53239
PCT Pub. Date: Sep. 14, 2000

(30) Foreign Application Priority Data

Mar. 9, 1999 (EP) .......................................... 99200688

(51) Int. Cl.$^7$ ............................................... A61N 1/362
(52) U.S. Cl. ....................................................... 600/18
(58) Field of Search ..................... 600/16–18; 604/6.11, 604/43, 103.07, 103.08, 523–528

(56) References Cited

U.S. PATENT DOCUMENTS

| | | | |
|---|---|---|---|
| 4,406,656 A | * | 9/1983 | Hattler et al. |
| 4,762,130 A | * | 8/1988 | Fogarty et al. |
| 4,798,193 A | * | 1/1989 | Giesy et al. |
| 4,824,435 A | * | 4/1989 | Giesy et al. |
| 4,846,791 A | * | 7/1989 | Hattler et al. |
| 5,407,432 A | * | 4/1995 | Solar |
| 5,569,219 A | * | 10/1996 | Hakki et al. |
| 5,807,311 A | * | 9/1998 | Palestrant |
| 5,827,243 A | * | 10/1998 | Palestrant |
| 5,882,290 A | * | 3/1999 | Kume |
| 6,190,356 B1 | * | 2/2001 | Bersin |
| 6,533,716 B1 | * | 3/2003 | Schmitz-Rode et al. |

FOREIGN PATENT DOCUMENTS

| | | |
|---|---|---|
| DE | 298 04 046 | 4/1998 |
| WO | WO 97/07850 | 3/1997 |

* cited by examiner

*Primary Examiner*—Mark Bockelman
(74) *Attorney, Agent, or Firm*—Young & Thompson

(57) ABSTRACT

Invention relates to a cannula and a screw pump for use in a mechanical circulatory support device, in particular a transventricular circulatory support device. The cannula according to the present invention comprises a tubular member made of a flexible, collapsible material having a diameter between 0.5 cm and 3 cm, preferably between 1 cm and 2.5 cm. The invention also relates to an inflatable screw pump for use in circulatory support system which comprises a flexible central drive shaft and an inflatable body having a free edge defining a spiral shaped contour around the central drive shaft and an inner edge connected to the drive shaft. The Archimedes type screw pump may be used in conjunction with the flexible cannula. The method of connecting the circulatory assist device to the heart comprises the steps of introducing the distal end of a cannula into a large systemic vein or into the right or left atrium, guiding the distal end of the cannula via the atrium to the inflow valve of the ventricle, and from there into the ventricle, guiding the distal end of the cannula from the ventricle to the ventricle outflow valve and from there into the pulmonary artery, the aorta or a side branch of the aorta and, connecting the proximal end of the cannula to a pump.

15 Claims, 5 Drawing Sheets

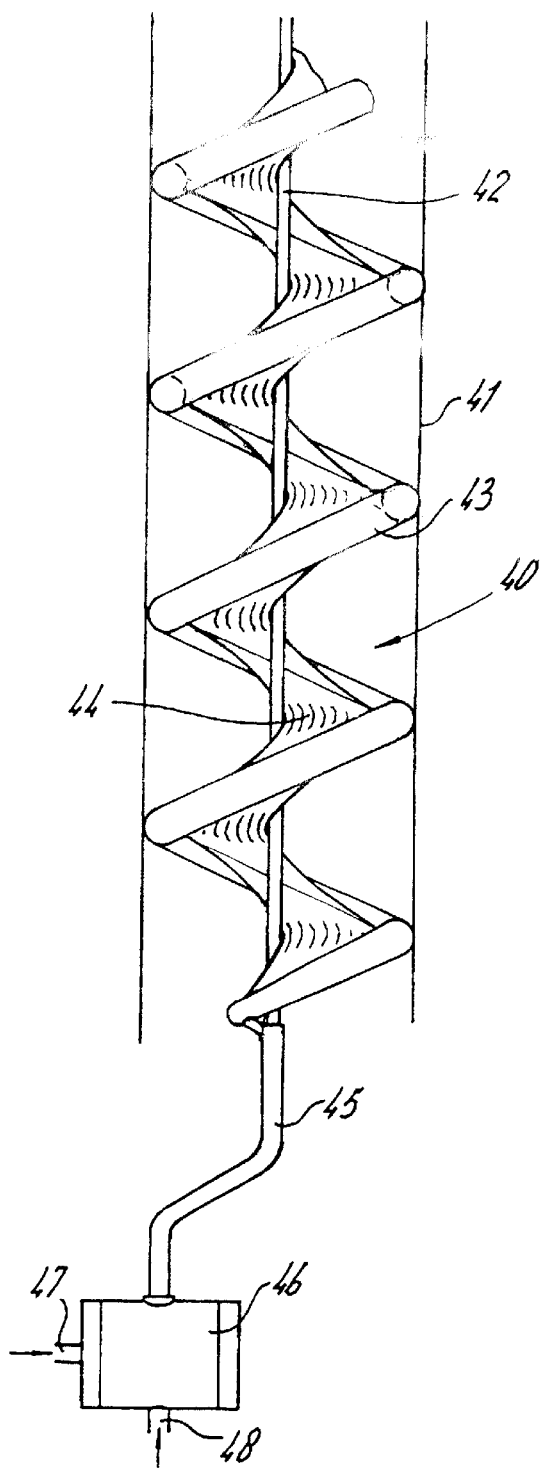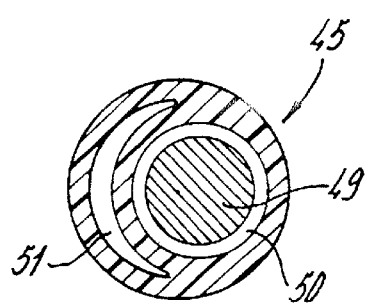

METHOD AND DEVICE FOR TRANSVENTRICULAR MECHANICAL CIRCULATORY SUPPORT

FIELD OF THE INVENTION

The invention relates to a cannula and a screw pump for use in a mechanical circulatory support device in particular a transventricular circulatory support device. The invention also relates to a method of providing mechanical transventricular support in open and closed chest approaches using said cannula and/or said screw pump.

BACKGROUND OF THE INVENTION

In the course of coronary artery bypass grafting (CABG) without the use of the classical heart-lung machine, it may be required to provide a mechanical circulatory support system to boost failing heart performance. During bypass grafting on the beating heart, occlusion of segments of coronary arteries can cause failure of the pump function of both heart chambers due to lack of oxygen in the heart muscle or due to arrhytmia. Displacing of the beating heart within the thorax to obtain access to the coronary anastomotic site of the heart, may also lead to mechanical interference with the pump function. This may require the temporary use of an auxiliary blood pump. Such a blood pump may be placed outside or inside the blood circulation. The right and left heart chambers form two pumps placed in series, which may each be assisted in their pump function by a right ventricle assist device (RVAD) and left ventricle assist device (LVAD), respectively.

For a right ventricle assist device (RVAD), the pump outside the circulation bypasses the blood flow that enters the right atrium and that passes from the right atrium via the right ventricle into the pulmonary trunc. Placement of the pump outside the circulation leads to two holes in the circulatory system, one access hole for the cannula that supplies blood from the venous side of the systemic circulation to the assist pump and a second access hole for the output cannula of the assist pump. The inflow cannula of the assist pump may be put in place via a stab wound in the right atrium or right ventricle wall, or via a puncture in a large systemic vein, such as the jugular or femoral vein. The outflow cannula of the assist pump can be placed distal to the right ventricular outflow valves e.g via a puncture hole in the pulmonary trunc. For a LVAD, the bypass connects the left atrium or left ventricle to the aorta, or may comprise an apical cannulation.

Different types of extra-corporeally placed assist pumps may be used, such as a DeBakey roller pump, continuous flow pumps such as centrifugal pumps and rotary blood pumps, pulsatile pumps, etc.

When the assist pump is used within the circulation, only a single access site is needed. An axial catheter-mounted screw pump, marketed by Johnson & Johnson of Warren, N.J. under the trade name HEMOPUMP, utilises a principle similar to that of an Archimedes screw. When used for left ventricle support, the screw element, which is placed inside a curved silicone rubber catheter, is positioned in the aorta, with the inlet in the left ventricle lumen. The pump assembly is made of stainless steel and has about the size of a pencil. The drive motor of the screw element is located extracorporeally, and drives the screw element at about 25000 rpm such that the pump draws a steady stream from the left ventricle. For right ventricle support, the pump can be inserted in the pulmonary artery through a stab wound, the inlet side being positioned in the lumen of the right ventricle.

The above methods of cannulation for the intra and extracorporeally placed assist pumps have several disadvantages. Firstly, access to the circulation is achieved through a cut in possibly calcified vessels. Secondly, the methods may result in dislodgement of plaque with consequent risk of embolisation. Thirdly, false air aspiration may occur at the cannulation site for blood withdrawal, with subsequent risk of air embolisation. Finally, in case a so-called "reverse hemopump" is used which is introduced into the circulation via one of the ventricles, or during cannulation of the apex of the left ventricle for a LVAD, a cut into the heart muscle may lead to bleeding complications.

It is therefore an object of the present invention to provide a cannula, a pump, and method of using the same in right or left transventricular mechanical support, which avoid the above drawbacks, and which allow for rapid placement through the least vulnerable tissues without the need of a cut in diseased blood vessels, such as a calcified ascending aorta or stenosed calcified peripheral arteries. It is a further object of the present invention to provide a cannula, pump and method of transventricular mechanical circulatory support in which cannulation of the large outflow vessels of the right and left ventricle (pulmonary trunc or artery and aorta, respectively) need not be cannulated, and which can be carried out in a minimally invasive manner, preferably under close chest conditions.

SUMMARY OF THE INVENTION

Hereto the cannula according to the present invention comprises a tubular member made of a flexible, collapsible material having a diameter between 0.5 cm and 3 cm, preferably between 1 cm and 2.5 cm. Preferably the material of the cannula is substantially non-extendible. When used as a RVAD, the cannula according to the present invention can be introduced into the right atrium via a cut into a larger vein, whereafter the distal end is introduced into the right ventricle via the tricuspid valve. The sharply curved trajectory at the apex of the right ventricle can be easily followed by the very flexible cannula of the present invention. From the right ventricle the flexible cannula is guided along the right ventricle outflow valve and is lodged with its distal (outflow) end in the pulmonary artery or pulmonary trunc. The inflow side of the cannula may be connected to an extra or intracorporeally situated bloodpump. The very flexible cannula, which upon insertion is collapsed to very small dimensions, may be inserted directly into the atrium during open or closed chest CABG or may be inserted in a peripheral vein (e.g. femoral or jugular or axillar vein) and advanced to a central location for blood delivery in the pulmonary artery. The assist pump may remain outside the chest. A similar procedure applies to the use of the cannula of the present invention for left ventricle assist devices (LVAD). A LVAD may form a bypass for drainage of blood from the left atrium and for blood delivery to the aorta. The flexible cannula may be introduced into the left atrium through the right upper pulmonary vein, or right atrium with subsequent perforation of the atrial septum, or via the left atrial roof or left atrial appendage.

A suitable material for the cannula comprises polymer (polyethane) angioplastic balloon material or polyurethane with a wall thickness of between 100 and 300 micrometer. Such material can easily drape and flex without being extendible, such that it can be collapsed to very small dimensions to be easily manipulated within the heart.

In a preferred embodiment the cannula comprises a first lumen of a relatively large diameter and a second lumen parallel to the first lumen, and of a smaller diameter. The second lumen may be formed by lengthwise sealing together opposite located walls of the flexible cannula. A flexible guiding catheter may be introduced in the smaller lumen for guiding the flexible cannula to its proper position and for serving as a guideline that provides shape stability to the flexible cannula in the axial direction. The end of the flexible cannula may comprise a guide element of relatively short length such as a rail runner, for receiving a guide wire therethrough. The guide element may comprise an internal thread such that the cannula may be transported by rotation of the threaded guide wire which propels the guide element.

In one embodiment, the flexible cannula comprises a balloon at or near the distal portion of the cannula which allows vacuum collapse of the proximal and mid portion of the cannula upon introduction. This prevents filling of the lumen of the cannula and subsequently volume trapping. When the cannula is placed in its proper position, the guide catheter and the balloon may be withdrawn from the vessel or, alternatively, the catheter may be left in place to serve as a backbone for providing longitudinal dimensional stability to the flexible cannula. The second lumen of the cannula surrounding the backbone catheter avoids stagnant flow areas and prevents direct blood contact with less biocompatible components of the catheter wire.

For attachment of the inflow side of the flexible cannula to a regular rigid cannula or to an intracorporeally located screw pump, the cannula may at its proximal end comprise a ring-shaped inflatable element which is provided with an inflation lumen. Upon inflation of the ring-shaped element, the proximal end of the flexible cannula is clampingly engaged with the rigid inflow cannula or with a screw pump attachment part.

Even though the flexible cannula according to the present invention may be used with a pump which is placed either inside or outside the blood circulation, it is preferred that it is used together with an Archimedes type screw pump having a flexible central drive shaft and an inflatable body having a free edge defining a spiral-shaped contour around the central drive shaft and an inner edge connected to the drive shaft. The inflatable Archimedes type screw pump may be attached to the inlet side of the cannula while its rotary drive shaft extends to outside the body where it is rotated by a motor drive unit This yields a completely transluminal ventricular assist system with an acceptable small diameter upon introduction and retrieval from a peripheral vessel and having a sufficiently large diameter after expansion of the inflatable Archimedes type screw pump and the flexible cannula to deliver a blood flow at a rate of 2 liters per minute or more.

For RVAD blood delivery to the pulmonary trunc the inflatable Archimedes type screw pump may be inserted through the peripheral access through femoral, jugular or axillar vein, or transthoracally through a key hole access directly into the right atrium. For LVAD, (blood delivery to the ascending aorta), the right upper pulmonary vein, or the atrial appendage or the roof of the left atrium or the left ventricular apex may be stabbed directly in the open chest or closed chest approach. Alternatively, for LVAD, access to the left heart side may be reached from the venous circulation using the latter access and by subsequently perforating the wall (atrial septum) between the right and left atrium.

BRIEF DESCRIPTION OF THE DRAWINGS

The invention will be explained in detail with reference to the accompanying drawings. In the drawings:

FIG. 5 shows a ventricular assist device according to the present invention including an inflatable Archimedes type screw pump attached to the proximal end of a flexible cannula, FIG. 6 shows a cross-sectional view of the drive shaft of an inflatable Archimedes screw pump according to the present invention.

DETAILED DESCRIPTION OF THE INVENTION

Figure 1:
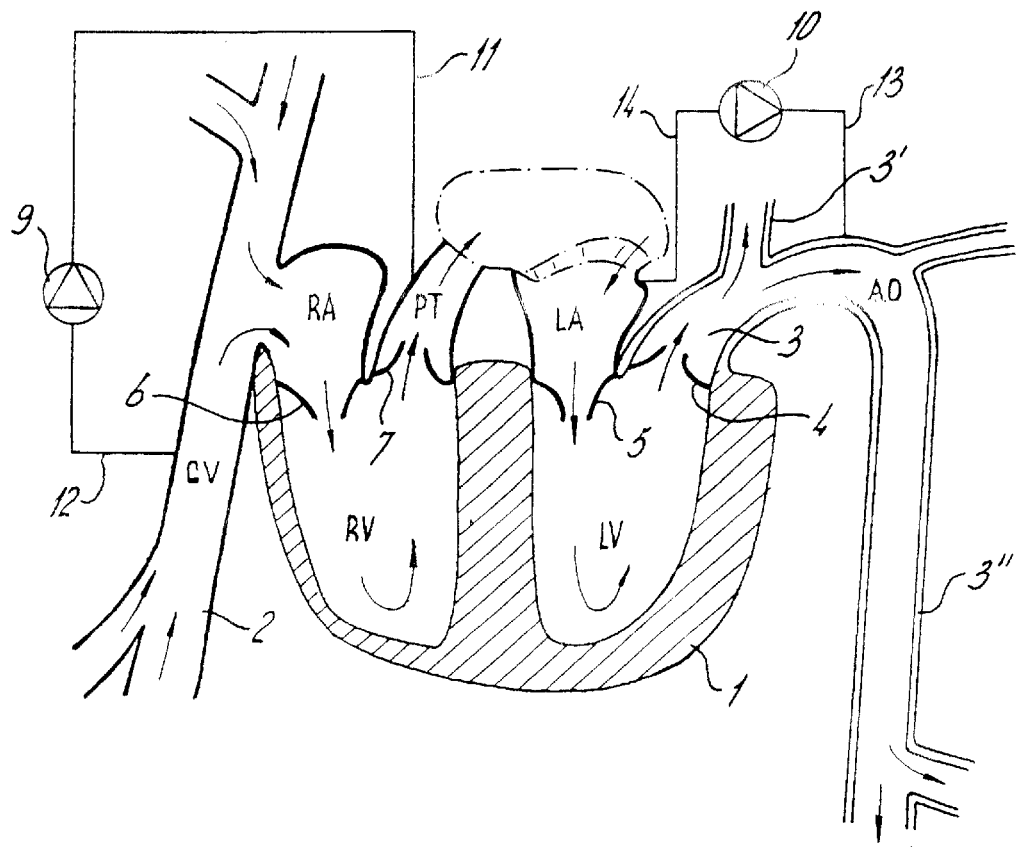
FIG. 1 shows a schematic cross-sectional view of the anatomy of the heart including a RVAD, and a LVAD.

In FIG. 1 a schematic representation of the basic anatomy of the heart is shown, showing parallel assisted pumping using a right extracorporeally located ventricular assist device (RVAD) and a left extracorporeally located ventricular assist device (LVAD). The arrows indicate the direction of the blood flow. The RVAD comprises a pump 9 which bypasses the blood circulation normally flowing from large systemic veins (caval veins, CV) into the right atrium (RA), via the right ventricle inflow valve or tricuspid valve 6 into the right ventrical (RV). The bypass of the RVAD connects the caval veins (CV) or the right atrium with the pulmonary trunc (PT) or with the pulmonary artery. From the right ventricle the blood flow passes via the right ventricle outflow valve 7 into the pulmonary trunc and from there into the lungs and from the lungs back into the left atrium (LA) via the mitral valve 5 into the left ventrical (LV) and from thereon past the aortic valve 4 into the ascending aorta 3 and descending aorta 3" (AO).

For the right ventricle assist pump 9, the inflow side 12 may be attached to a large systemic vein, the right atrium RA (appendix) or to the right ventricle RV. The outflow side 11 of the RV assist pump 9 may be attached to the pulmonary trunc PT.

The LV assist pump 10 ma have its inflow side 14 connected to the left ventricle LV or to the left atrium LA. The outflow side 13 of the LV assist pump 10 may be connected to the ascending aorta 3, to the descending aorta 3" or to a large side branch 3'. The pumping rates of the assist pumps 9,10 are up to 3 L/min or 10 L/min for partial ventricular support (booster), depending on the requirements of the patient.

Figure 2:
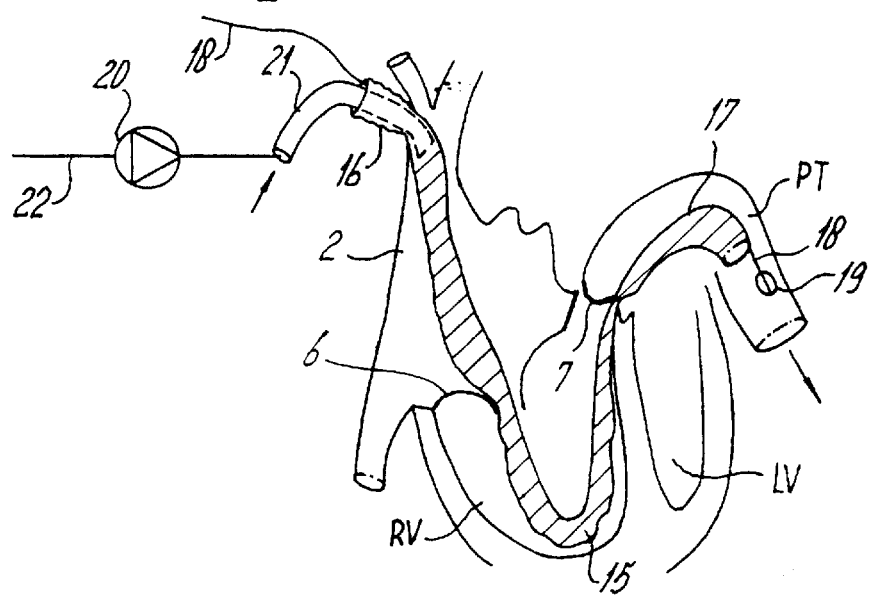
FIG. 2 shows a RVAD using a flexible cannula according the present invention.

FIG. 2 shows the intraventricular trajectory of the cannula according to the present invention, in particular when used as a transventricular mechanical circulatory support system. The flexible cannula 15 extends along the sharply curved trajectory of the right ventricle RV and has its outflow side located in the pulmonary trunc for blood delivery to the lung circulation in combination with unloading the right ventricle RV. The cannula 15 is introduced to the venous circulation through a cut in the superior caval vein (CV), one of its side branches or in the right atrial tissue. Flexible cannula 15 is provided with a Swan-Ganz guiding catheter 18 which acts a backbone catheter and which its end is provided with an inflatable balloon 19. When the outflow portion at the distal end 17 of the cannula 15 has reached its position of optimal placement in the pulmonary artery beyond the pulmonary valve, a rigid preformed cannula 21 is inserted into the proximal end of the cannula 15, which cannula 21 is connected to the outflow side of assist pump 20. The heart valves 6 and 7 fold over the easily collapsible material of the cannula 15. The collapsible cannula 15 is in its collapsed mode no obstruction to normal intracardiac flow when the assist pump 20 is riot activated. The inflow side 22 of the pump 20 may be connected to a second cannula which is not shown in the drawing and which may be inserted in the venous circulation.

Figure 3:
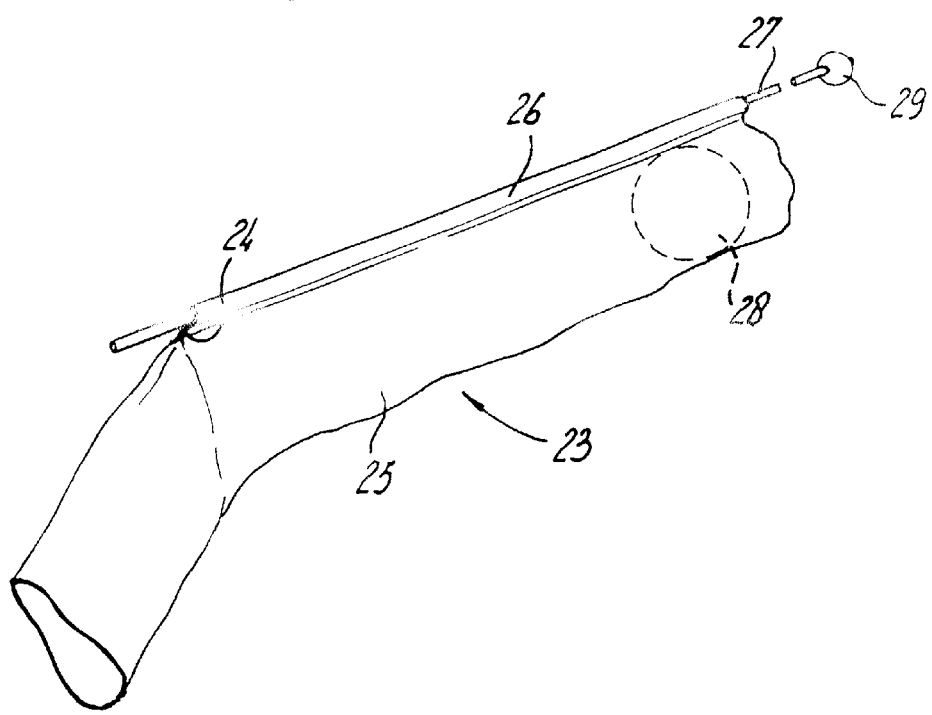
FIG. 3 shows the flexible cannula according to the present invention including a backbone catheter.

FIG. 3 shows an assembly of the flexible cannula 23 according to the present invention which is provided with a "backbone" or guiding catheter 27. The cannula 23 may have a length of between 15 and 30 centimeters and has a diameter of between 0,5 and 3 centimeter, preferably about 2 centimeter. The flexible cannula 23 is made of a PTE polymer material, angioplasty balloon material or polyurethane and has a wall thickness of between 100 and 300 micrometers. The cannula 23 comprises a lengthwise seal 24 along which the material of the walls of the cannula is fused. Thereby a first lumen 25 and a second lumen 26 are formed, which second lumen surrounds the guide catheter 27. The cannula 23 may exist of an ultra thin wall, non-extendible, highly flexible polymer such as for instance used for waste or refuse collection bags. When deployed, the cannula 23 cannot distend further by elastic deformation such that the positions of its proximal and distal ends are accurately defined, and that no overdistention, or ballooning occurs, with consequent risk of obstruction of native blood flow. The balloon tipped (balloon 29) backbone guiding catheter 27 is flexible and allows steering, similar to a diagnostic Swan-Ganz catheter. At its distal end, the cannula 23 is provided with an internal balloon 28 which allows vacuum collapse of the proximal and mid portion of the cannula 23 upon introduction, which prevents filling of the lumen 25 and subsequent volume trapping. The guide catheter 27 is provided with an additional inflation lumen ending at the balloon 28. After the cannula 23 has been introduced into the circulation, the cannula 23 is unfolded by increasing the pressure at the inlet by supplying blood or a saline solution, so that it assumes its tubular shape. When the cannula is in its required position, the balloon 28 is deflated to open the outflow end of the cannula.

Figure 4:
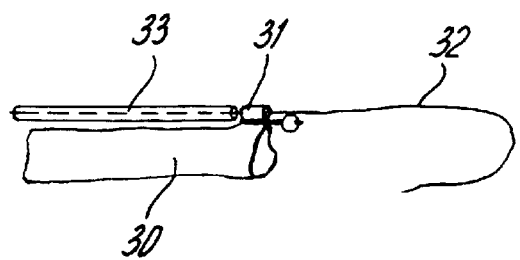
FIGS. 4 shows a method of introducing the cannula according to the present invention along a guide rail.

FIG. 4 shows an embodiment wherein the flexible cannula 30 is at its distal end provided with a rail runner 31 which is placed around the guide wire 32. The guide wire 32 may first be placed in the circulation along the curved trajectory through the heart. Thereafter the rail runner 31 at the distal end of cannula 30 is placed over the guide wire and is thereafter pushed forward by a tube 33 which is placed over the guide wire 32. In this way the flexible cannula 30 is pushed forward and can be finally positioned. In an alternative embodiment the rail runner 31 may contain an internal screw thread and the guide wire 32 may be provided with an external screw thread. By rotation of the guide wire 32, the rail runner 31 can be moved ahead.

FIG. 5 shows an assembly comprising a flexible cannula 41 and located therein an inflatable Archimedes type screw pump 40. The screw pump 40 comprises a flexible central drive shaft 42, which is for instance made of a flexible braiden metal wire. The screw pump 40 comprises a spirally wound inflatable tube 43 which is via a membrane 44 connected to the central drive shaft 42. Inflatable tube 43 is connected to a lower drive shaft 45 which is hollow and which comprises a central flexible drive shaft, a lubrication and cooling channel surrounding the central drive shaft and a separate saline inflation and deflation channel. The lower drive shaft 45 is rotatably connected to a motor unit 46 comprising a lubrication and cooling port 48 and an inflation/deflation saline port 47.

In the deflated state, the screw pump 40 will collapse and assume a relatively low profile which will allow insertion and retrieval through a relatively small puncture hole. The material of the membrane 44 and the tubular body 43 may be Percutanous Transluminal Coronary Angioplasty (PTCA) balloon skin material which may withstand pressures of up to 30 bar. Inflation of the tubular body 43 with saline to pressures up to 30 bar will stretch the screw pump 40 longitudinally as well as radially such that it assumes its Archimedean shape, with a diameter of the screw pump of between 0.5 and 3 cm, preferably about 2 cm. During rotation, the PTCA balloon skin material does not stretch. Due to its large wall tension, the tubular body 43 will form a stiff structure suitable for pumping blood at rates of 2 liters per minute or more at relatively low rotational speeds such as speeds of 1000 rpm. To create a forward flow, the inflated screw element formed by the inflatable tubular body 43 and the membrane 44 may rotate within the stationary cylinder formed by cannula 41.

FIG. 6 shows a cross-sectional view of the lower part 45 of the drive shaft 42 wherein a central drive wire 49 which is surrounded by a lubrication and cooling channel 50. A separate saline inflation channel 51 is incorporated in the wall of the lower drive shaft 45.

Figure 7:
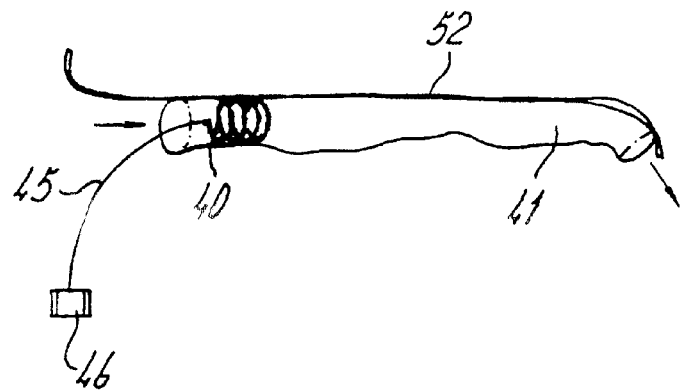
FIG. 7 shows an assembly of the flexible cannula having its proximal end attached to an inflatable Archimedes type screw pump according to the present invention.

FIG. 7 shows an integrated unit comprised of the flexible cannula 41 into the proximal end of which an Archimedean screw pump 40 is positioned. The rotary blood pump 40 may be electrically, pneumatically or externally cable driven such as shown in the figure, by the lower part 45 of the drive shaft 42 which is connected to an extracorporeally placed motor unit 46. In position, the length dimension of the flexible cannula 41 is stabilised by backbone catheter 52.

Figure 8:
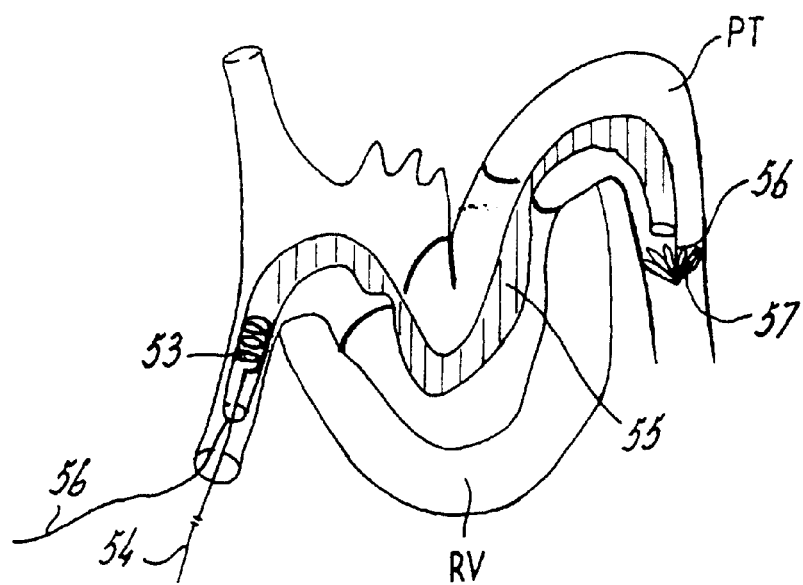
FIG. 8 shows the intra ventricular course of the assembly of the Archimedes type screw pump and flexible cannula when used as a RVAD.

FIG. 8 shows the transventricular application of an assembly consisting of the flexible cannula. 55 which contains in its proximal end Archimedes type screw pump 53. Then lower part 54 of the rotary drive shaft, as well as a backbone catheter 56 extend through the venous system to outside the patient's body. At its distal end, the cannula 55 may be anchored into the pulmonary trunc PT by means of an inflatable anchoring mechanism 57, which allows unrestricted introduction of the cannula and an easy passage past the heart valves.

Figure 9:
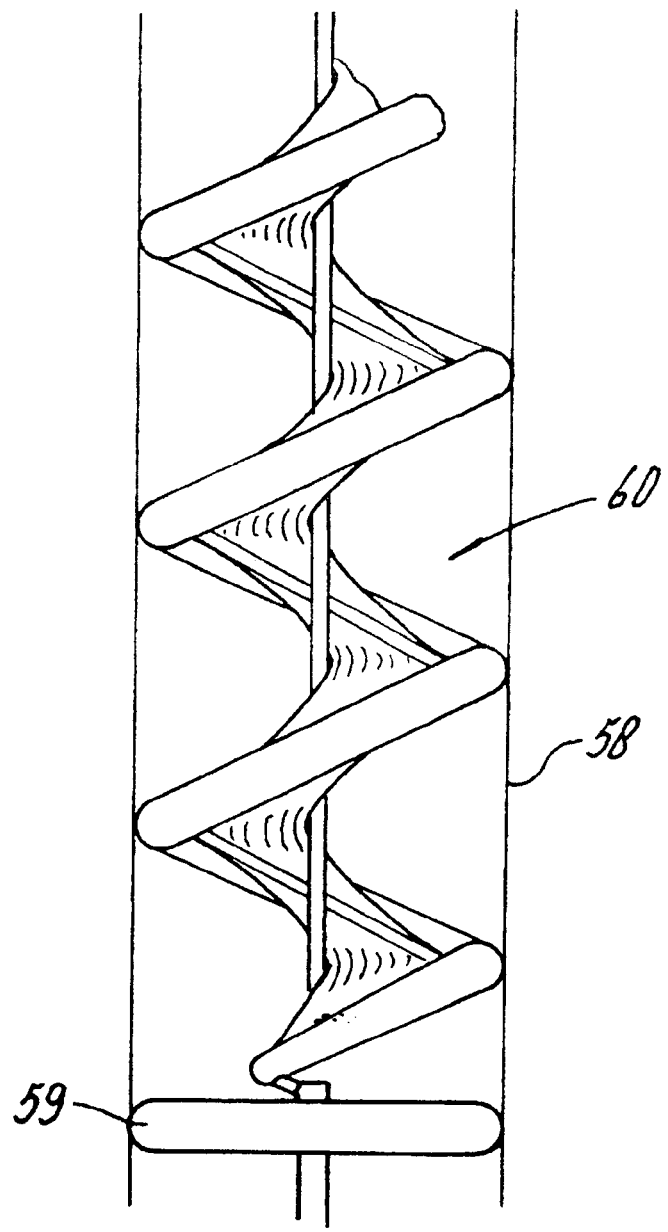
FIG. 9 shows the attachment of the flexible cannula to the Archimedes type screw pump.

In the embodiment shown in FIG. 9, the flexible cannula 58 comprises at its proximal end an inflatable ring-shaped element 59 which will prevent collapse of the proximal end of the cannula upon suction created by the rotation of the Archimedes type screw pump 60. The inflatable screw 60 end the flexible cannula 58 may be introduced together through a two-way introducer with saline flush as its third port. The tip of the screw 60 has to be lodged into the folded cannula 58 outside the vascular access site, but inside the introducer, which thereto is preferably transparent.

In Vitro Experiment

The flexible cannula according to the present invention (length 40 cm, expanded diameter approximately 12 mm)

was connected to a fluid pump. The device was coiled up twice and was torqued in the longitudinal direction to mimic the pathway through a sharply bended trajectory. Water flow exceeded 7 L/min while the pressure gradient over the cannula did not exceed 100 mm Hg. The cannula uncoiled, untwisted, unfolded and fully expanded spontaneously under pressurized water supply.

In Vivo Experiments

Five acute experiments in the living pig (80 kg) have been performed. Cannulation for the implementation of right heart bypass using the flexible cannula according to the present invention were tested in two different access sites, i.e. central cannulation through the right atrial appendage (n=1) and introduction through a peripheral vein (n=4). An extracorporeally located blood pump was used as right ventricular assist device and connected to the flexible cannula. The heart was exposed by splitting the sternal bone. For blood withdrawal to the blood pump, the venous circulation was cannulated in the classical fashion.

Central access. The introduction of the flexible cannula through the right atrial appendage and placement in the pulmonary artery was accomplished. Bypass flow exceeded 2 L/min.

Peripheral access. The right jugular vein was exposed and was punctured for the introduction of the flexible cannula. In all four cases cannula placement was accomplished successfully without adverse effects. Introduction time was eventually <5 minutes. Bypass flow exceeded 4 L/minute while the right ventricle was visibly decompressed. In displaced beating heart, mechanical assistance of the right ventricle normalized the systemic circulation. Control fluroscopy revealed a transit ventricular position of the cannula and deposition of contrast medium in the pulmonary artery beyond the pulmonary valve without signs of valvular incompetence. Post-mortem examination showed that the cannula was situated correctly in the right ventricle ie passage through the tricuspid valve, the right ventricle lumen and the pulmonary valve. The tip was located in the pulmonary trunc. In no case trombosis was noted. In one additional case the cannula was introduced through the left atrial appendage and placed in the left ventricle.

What is claimed is:

1. Cannula for use in a circulatory support system comprising a tubular member made of a flexible, collapsible material having a proximal inflow opening and a distal open end and having a diameter between 0.5 cm and 3 cm, wherein the cannula is made of a substantially non-extendible plastic polymer sheet material and comprises a first lumen of a relatively large diameter and a second lumen parallel to the first lumen, the second Lumen having a smaller diameter for receiving a flexible guide wire element.

2. Cannula (15, 23, 30, 41, 55, 58) according to claim 1, wherein the cannula has a wall thickness of between 50 and 500 micrometer, preferably between 100 and 300 micrometer.

3. Cannula (23) according to claim 1, wherein at the boundary (24) between the first and second lumen, the opposite walls of the tubular member are connected along a sealing line that is offset from the center line of the tubular member.

4. Cannula (30) according to claim 1, wherein the second lumen forms a guide element (31) at a distal end of the cannula, which is of a relatively short length compared to the length of the cannula, for receiving the guide wire element (32) therethrough.

5. Cannula (30) according to claim 4, wherein the guide element (31) comprises an internal thread.

6. Cannula (23) according to claim 1, comprising at or near a distal end an internal inflatable element (28), connected to the walls of the tubular member and connected to an inflation lumen, for collapsing a part of the cannula.

7. Cannula (58) according to claim 1, the cannula being at its proximal end provided with a ring-shaped inflatable element (59) which is connected to the wall of the tubular member and which is coaxially located with respect to said tubular member, the inflatable element (59) being connected to an inflation lumen.

8. Assembly comprising a cannula (23) according to claim 1, and a catheter (27, 56) extending through the second lumen (26), the catheter (27, 56) comprising at its distal end an inflatable element (29, 57).

9. Assembly according to claim 8, wherein the inflatable element comprises an anchoring device (57) for anchoring the distal end of the cannula (23) in a blood vessel.

10. Cannula according to claim 1, wherein the cannula has a diameter between 1 cm and 2.5 cm.

11. Circulatory assist device comprising a cannula according to claim 1, and a screw pump element comprising:
a flexible central drive shaft,
a tubular inflatable body defining, when inflated, a spiral-shaped contour around the central drive shaft, and
a membrane connecting the tubular body to the drive shaft, the membrane extending along the entire tubular body and spirally around the drive shaft, the screw pump element being located inside the cannula.

12. Method of connecting a circulatory assist device to the heart, in particular a ventricular assist device, comprising the steps of:

introducing the distal end of a cannula according to claim 1, into a blood vessel or into the left or right atrium;
guiding the distal end of the cannula via the atrium to the inflow valve of the ventricle, and from there into the ventricle;
guiding the distal end of the cannula from the ventricle to the ventricle outflow valve and from there into the pulmonary artery or the aorta; and
connecting the proximal end of the cannula to a pump.

13. Method according to claim 12, wherein a screw pump, having a flexible central drive shaft (42), and an inflatable body (43) having a free edge defining a spiral-shaped contour around the central drive shaft, and an inner edge connected to the drive shaft, is introduced together with the cannula or subsequent to placement of the cannula, in its deflated state, to be located inside the cannula at the proximal end thereof, the screw pump being thereafter inflated and rotated via the flexible drive shaft from an extracorporeally located drive motor.

14. Screw pump element for use in a circulatory support system, comprising:

a flexible central drive shaft,
an inflatable tubular body defining, when inflated, a spiral-shaped contour around the central drive shaft, and
a membrane connecting the tubular body to the drive shaft, the membrane extending along the entire tubular body and spirally around the drive shaft.

15. Screw pump element according to claim 14, wherein the flexible drive shaft (45) at the proximal end of the inflatable body (43) comprises an inflation/deflation channel (51).

* * * * *